United States Patent
Arvanian et al.

(10) Patent No.: US 9,623,107 B2
(45) Date of Patent: Apr. 18, 2017

(54) METHODS OF TREATING NEURODEGENERATIVE CONDITIONS

(71) Applicant: The Research Foundation for The State University of New York, Albany, NY (US)

(72) Inventors: Victor L. Arvanian, Huntington, NY (US); Joel M. Levine, Miller Place, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 14/818,013

(22) Filed: Aug. 4, 2015

(65) Prior Publication Data
US 2016/0030560 A1 Feb. 4, 2016

Related U.S. Application Data

(60) Provisional application No. 62/032,830, filed on Aug. 4, 2014.

(51) Int. Cl.
*C12N 15/86* (2006.01)
*A61K 39/395* (2006.01)
*C12N 7/00* (2006.01)
*A61K 9/00* (2006.01)
*C07K 16/44* (2006.01)
*A61K 39/00* (2006.01)
*A61K 48/00* (2006.01)

(52) U.S. Cl.
CPC ........ *A61K 39/3955* (2013.01); *A61K 9/0085* (2013.01); *C07K 16/44* (2013.01); *C12N 7/00* (2013.01); *A61K 48/00* (2013.01); *A61K 2039/525* (2013.01); *A61K 2039/54* (2013.01); *C12N 2750/14143* (2013.01); *C12Y 402/02004* (2013.01)

(58) Field of Classification Search
None
See application file for complete search history.

(56) References Cited

PUBLICATIONS

Ruitenberg et al., Methods vol. 28 (2002) pp. 182-194.*
Hunanyan et al., J. Neurophysiol vol. 110 (2013) pp. 1782-1792.*

* cited by examiner

*Primary Examiner* — Jim Ketter
(74) *Attorney, Agent, or Firm* — Scully, Scott, Murphy & Presser, P.C.

(57) ABSTRACT

The present disclosure is directed to adeno-associated viral vector monoclonal antibody constructs and compositions thereof, methods of improving locomotor function after spinal cord injury, methods of treating neurodegenerative diseases.

10 Claims, 17 Drawing Sheets

SEQUENCE LISTING

```
<160> NUMBER OF SEQ ID NOS: 2

<210> SEQ ID NO 1
<211> LENGTH: 795
<212> TYPE: DNA
<213> ORGANISM: Artificial Sequence
<220> FEATURE:
<223> OTHER INFORMATION: Mab69 single chain antibody

<400> SEQUENCE: 1
atggcgtggg tgtggaccct gccgtttctg atggcggcgg cgcagagcat tcaggcgcag      60
attcagctgg tgcagagcgg cccggaactg atgaaaccgg gcgaaaccgt gcgcattagc     120
tgcaaagcga gcggctatac ctttaccgat tatagcatgc attggatgcg ccagggcccg     180
ggcaaagtgc tgaaatggat ggcgtggatt aacaccgaaa ccggcgaacc gacctatgcg     240
gatgatttta aaggccgctt tgcgtttagc ctggaaacca gcgcgagcac cacctttctg     300
```

```
cagattaaca gcctgaaaaa cgaagatacc gcgacctatt tttgcagccg cggcgatagc    360
tttgcgtatt ggggccaggg caccctggtg accgtgagcg cgggcggcgg cggcagcggc    420
ggcggcggca gcggcggcgg cggcagcgat accattctga cccagacccc gtttagcctg    480
ccggtgagcc tgggcgatca ggcgagcatt agctgccgca gcagccagcg cctggaaaac    540
agcaacggca acacctatct gaactggtat gtgcagaaac cgggccagag cccgcagctg    600
ctgatttatc gcattagcaa ccgctttagc ggcgtgctgg atcgctttag cggcagcggc    660
agcggcaccg attttaccct gaaaattagc cgcgtggaag cggaagatct gggcgtgtat    720
ttttgcctgc agctgaccca tgtgccgtat acctttggcg gcggcaccaa actggaaatt    780
aaacgcgcgc tggaa                                                     795
```

```
<210> SEQ ID NO 2
<211> LENGTH: 265
<212> TYPE: PRT
<213> ORGANISM: Artificial Sequence
<220> FEATURE:
<223> OTHER INFORMATION: Mab69 single chain antibody

<400> SEQUENCE: 2

Met Ala Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Met Lys
            20                  25                  30

Pro Gly Glu Thr Val Arg Ile Ser Cys Lys Ala Ser Gly Tyr Thr Phe
        35                  40                  45

Thr Asp Tyr Ser Met His Trp Met Arg Gln Gly Pro Gly Lys Val Leu
    50                  55                  60

Lys Trp Met Ala Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Thr Phe Leu Gln Ile Asn Ser Leu Lys Asn Glu Asp Thr Ala Thr
            100                 105                 110

Tyr Phe Cys Ser Arg Gly Asp Ser Phe Ala Tyr Trp Gly Gln Gly Thr
        115                 120                 125

Leu Val Thr Val Ser Ala Gly Gly Gly Ser Gly Gly Gly Gly Ser
    130                 135                 140

Gly Gly Gly Gly Ser Asp Thr Ile Leu Thr Gln Thr Pro Phe Ser Leu
145                 150                 155                 160

Pro Val Ser Leu Gly Asp Gln Ala Ser Ile Ser Cys Arg Ser Ser Gln
                165                 170                 175

Arg Leu Glu Asn Ser Asn Gly Asn Thr Tyr Leu Asn Trp Tyr Val Gln
            180                 185                 190

Lys Pro Gly Gln Ser Pro Gln Leu Leu Ile Tyr Arg Ile Ser Asn Arg
        195                 200                 205

Phe Ser Gly Val Leu Asp Arg Phe Ser Gly Ser Gly Ser Gly Thr Asp
    210                 215                 220

Phe Thr Leu Lys Ile Ser Arg Val Glu Ala Glu Asp Leu Gly Val Tyr
225                 230                 235                 240

Phe Cys Leu Gln Leu Thr His Val Pro Tyr Thr Phe Gly Gly Gly Thr
                245                 250                 255

Lys Leu Glu Ile Lys Arg Ala Leu Glu
            260                 265
```

METHODS OF TREATING NEURODEGENERATIVE CONDITIONS

CROSS-REFERENCE TO RELATED APPLICATIONS

The present application claims benefit of U.S. Provisional Application 62/032,830, filed on Aug. 4, 2014, the contents of which are incorporated by reference.

GOVERNMENT SPONSORSHIP

This application was supported by grants from the Department of Defense (DOD SCO90068). The Government has certain rights in this application.

INCORPORATION BY REFERENCE OF SEQUENCE LISTING

The Sequence Listing in the ASCII text file, named as 31281_SequenceListing.txt of 4 KB, created on Aug. 4, 2015, and submitted to the United States Patent and Trademark Office via EFS-Web, is incorporated herein by reference.

BACKGROUND OF THE DISCLOSURE

Spinal cord injuries (SCI) and diseases are continuing medical conditions without adequate treatment options.

Within the central nervous system many pathological neurological conditions, including spinal cord injuries, involve altered function of not only neurons but also macrophages and glial cells, including oligodendrocytes and astrocytes. Studies suggest that glial response to the injury participates in formation of the astroglial scar and development of the "hostile" environment at the injury epicenter. Increased levels of inhibitory factors in and around the glial scar in damaged spinal cord are known to contribute to: (i) neuronal death that progresses during the course of secondary injury, (ii) restricted regeneration of damaged axons, (iii) disrupted myelination of lesioned and survived axons, and (iv) limited transmission through the surviving axons. These deficits are major burdens that restrict recovery of function following spinal cord injury or disease.

The role of glia in SCI is dual. They may contribute to secondary damage or be neuroprotective. The major glial response to SCI includes: (i) secretion of glia-derived scar-related inhibitory factors, such as chondroitin sulphate proteoglycans (CSPGs), including NG2, a major inhibitory factor restricting axonal regeneration and blocking axonal conduction, (ii) changes in transition of oligodendrocyte precursor cells (OPCs, known to be NG2-positive) into mature oligodendrocytes, thus effecting axonal myelination and remyelination, (iii) functional changes in astrocytes (i.e. reactive astrogliosis), which are major contributors to glial scar and known to secrete both growth promoting and inhibitory factors after SCI, (iv) activation of microglia, the number of which is rapidly elevated in the vicinity of the injury. Another cell type, macrophages, also accumulate close to the injury epicenter, and are known to be derived from both microglia and haematogenous macrophages. In many cases these cells are referred to as macrophages/microglia because it is difficult to discriminate between the activated microglia and macrophages in the injured central nervous system (CNS). Macrophages/microglia are among the major cells participating in the inflammatory cell response following SCI.

What is desired is a suitable method of improving spinal cord functionality after injury or disease. Embodiments of the present disclosure provide methods that address the above and other issues.

SUMMARY OF THE DISCLOSURE

The present disclosure is directed to adeno-associated viral vector monoclonal antibody constructs and compositions thereof, methods of improving locomotor function after spinal cord injury, methods of treating neurodegenerative diseases.

BRIEF DESCRIPTION OF THE DRAWINGS

The present disclosure will be better understood by reference to the following drawings of which:

FIG. 2a is a representative fluorescent image of spinal cord horizontal T9-T11 section taken at intermediate grey matter from rat injected with AAV-rh10-gfp (lighter color) viral vector and immunostained with neuronal marker NeuN (darker color). Note numerous NeuN positive cells expressing. FIG. 2b is a summary of results demonstrating number of transduced neurons per section at different spinal level. The number of transduced neurons was calculated by counting all cells that were both GFP positive and immunostained with NeuN throughout each cross-section. Data are derived from 5 sections 80 µm apart for each spinal level and presented as mean±SEM. (n=5 for AAV-5, AAV-9 and AAV-rh10; n=4 for AAV-1; n=3 for AAV-hu11). Scale bar is 100 µm.

FIGS. 3A and 3B are representative fluorescent image of thoracic T7 (3A) and lumbar L2 (3B) transverse sections taken from rat that received T10 contusion and intraspinal injections of AAV-rh10 serotype. FIG. 3C is a summary of results demonstrating GFP mean intensity per neuron calculated at different spinal levels. Results were obtained from maximum of 10 randomly selected transduced cells with neuronal morphology in grey matter per section. FIG. 3D is a summary of results demonstrating transduction area per individual section. Results are presented as percent of GFP positive area (neurons, processes and glial cells) vs. total area of section for each individual section. Data presented as mean±SEM. (n=5 for AAV-5, AAV-9 and AAV-rh10; n=4 for AAV-1; n=3 for AAV-hu11).

(FIG. 4A) anti-NeuN to detect neurons (intact grey matter caudal to injury epicenter, section form ventral horn), (FIG. 4B) anti-CD68 (ED1) to detect macrophages/microglia (injury epicenter, section from intermediate level), (FIG. 4C) anti-APC(CC1) to detect oligodendrocytes (intact lateral white matter just caudal to injury epicenter, section from intermediate level), (FIG. 4E) anti-NG2 to detect NG2 positive cells/processes (intact lateral white matter just caudal to injury epicenter, section from intermediate level) and (FIG. 4D) anti-GFAP to detect astrocytes (intact dorsal funiculus just caudal to injury epicenter). Left column: GFP positive cells and processes transduced with AAV-rh10-gfp (lighter color). Middle column: cells immunolabeled with each cell specific antibody used (darker color). Right column: merged images demonstrating GFP positive cell bodies and processes co-labeled with cell specific antibodies. Scale bars are 50 µm (note smaller magnification used for neurons).

FIG. 5A is a fluorescence image of horizontal T9-T11 spinal section at injury epicenter, from AAV-rh10-gfp (lighter color) injected animal and immunostained with ED1 (darker color); numerous cells positive for both GFP and ED1, demonstrating robust transduction of macrophages/microglia (injury epicenter, section from intermediate level). FIGS. 5B and 5C are summaries of results demonstrating best transduction of macrophages/microglia and oligodendrocytes induced by AAV-rh10 compared with other AAV serotypes. Results for ED1 are presented as % of area containing both GFP-positive and ED1-positive cells (after eliminating background as discussed below) vs. total area of ED1-positive cells within fixed area covering most of injury epicenter for each section; area and not number of cells was used for these measurements because of difficulty calculating the exact number of small-size ED1 labeled cells. Results for oligodendrocytes are presented as % of GFP-positive cells immunolabeled with CC1 vs. total number of CC1-positive cells within fixed area of white matter at T9 and T11 segments (i.e. just rostral and caudal to injury). Data presented as mean±SEM. (n=5 for AAV-5, AAV-9 and AAV-rh10; n=4 for AAV-1; n=3 for AAV-hu11). Scale bar is 50 µm.

FIGS. 6A and 6B are the summary of results demonstrating no significant difference in BBB score (6A) and body weight (6B) between control group that received contusion SCI and no injections and groups injected with different AAV serotypes following contusion SCI. FIG. 6C is a representative image of T9-T11 horizontal section following T10 contusion and AAV-rh10 intraspinal injections, immunostained with ED1 demonstrating typical macrophage/microglia immunoreactivity at the injury epicenter. FIG. 6D is a summary of results demonstrating no significant difference in ED1 immunoreactivity in rats with spinal cord injury and intraspinal injections of different AAV serotypes and rats with spinal cord injury and no AAV injections. Data presented as mean±SEM. (n=5 for AAV-5, AAV-9 and AAV-rh10; n=4 for AAV-1; n=3 for AAV-hu11). Scale bar is 100 µm.

DETAILED DESCRIPTION OF THE DISCLOSURE

Figure 1:
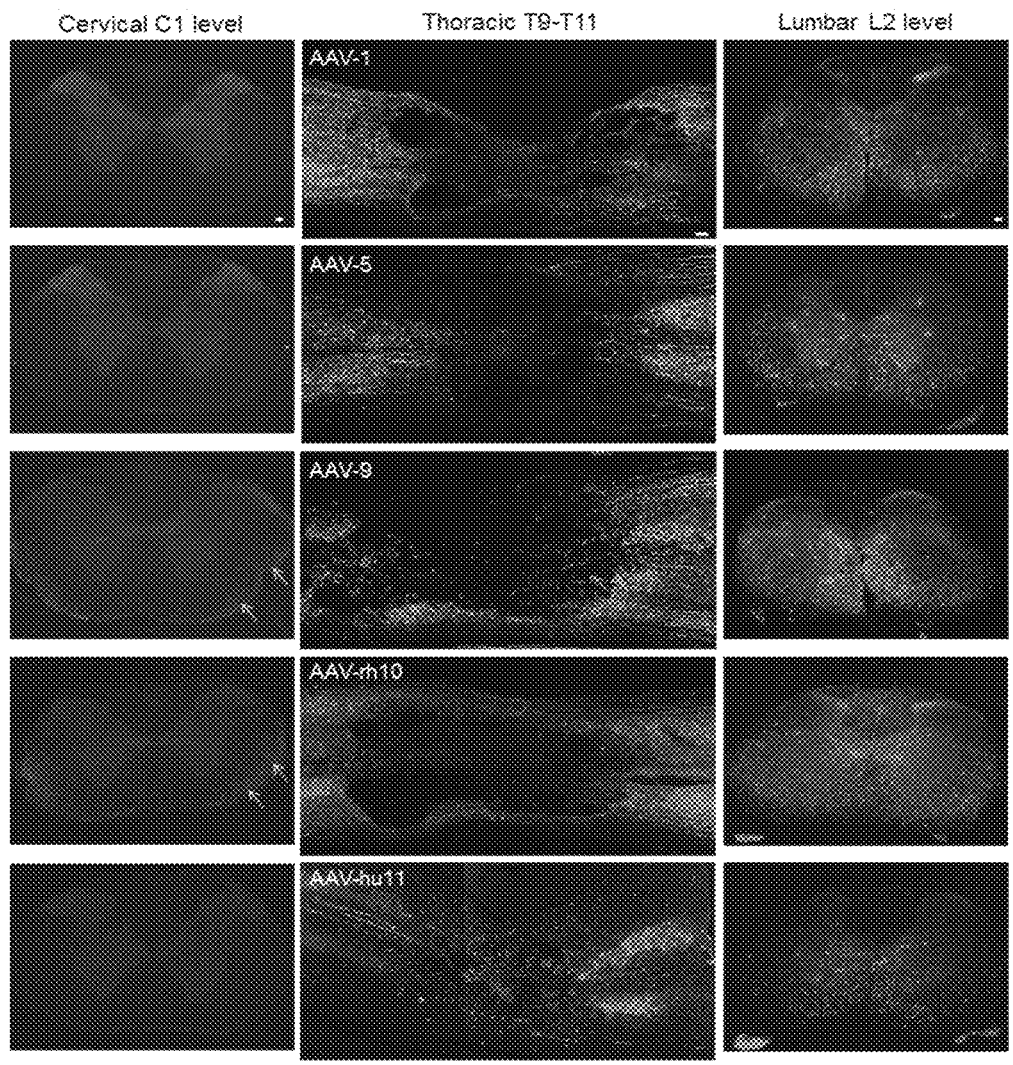
FIG. 1 includes representative images demonstrating transduction efficiency of AAV-1, 5, 9, rh10, hu11 serotypes at different spinal levels following intraspinal injections of these vectors after T10 contusion SCI. Representative fluorescent images of transverse cervical C1 and lumbar L2, and horizontal thoracic T9-T11 sections prepared 10 weeks following SCI and AAVs administration. Horizontal T9-T11 images consist of combined two images from same section. Scale bar is 100 µm.

The term "treat" as used herein refers to preventing, ameliorating, controlling, or curing the desired conditions, symptoms or disorders.

A "subject" is a mammal suffering from a disorder or injury or condition associated with a disorder or injury. The subject may be any kind of mammal, including human, canine, feline, equine, bovine, and rodent.

The term "therapeutically effective amount" refers to a dose sufficient to provide concentrations high enough to impart a beneficial effect on the recipient thereof. The specific therapeutically effective dose level for any particular mammal will depend upon a variety of factors including the disease, disorder or injury being treated, the severity of the disease, disorder or injury, the activity of the specific administered dose, the route of administration, the rate of clearance of the compound, the duration of treatment, the drugs used in combination or coincident with the compound, the age, body weight, sex, diet and general health of the subject, and like factors known in the medical arts and sciences.

The present disclosure relates to the use of adeno-associated viruses (AAVs) for therapeutic delivery to neurons in the treatment of various neurodegenerative disease including spinal cord injuries (SCIs), multiple sclerosis, and other glial related diseases.

AAV-rh 10 effectively transduces both neuronal and glial cells. AAV-rh10 surprisingly and unexpectedly transduces macrophages/microglia and oligodendrocytes in damaged spinal cords compared with efficacy of other AAV serotypes, such as AAV-1, AAV-5 and AAV9. AAV-rh10 and AAv-hu11 can both effectively transduce spinal cord tissue, including cells in gray matter and processes in white matter. Thus, one aspect of this disclosure is directed to treating neurodegenerative disease in a subject in need thereof comprising the administration of at least one adeno-associated virus selected from the group consisting of AAV-1, AAV-5, AAV-9, AAV-rh10 and AAV-hu11 and a pharmaceutically acceptable carrier.

AAV-rh10-mediated delivery of Neurotrophin 3 (NT3) combined with chondroitinase-ABC by intraspinal injections immediately following T10 contusion spinal cord injury (SCI) can improve anatomical plasticity, synaptic transmission and induce the appearance of detour synaptic pathways innervating dorsomedial interneurons. Animals treated with AAV-rh10-NT3/chondroitinase-ABC, following contusion SCI showed improved locomotor function, as discussed in the examples below. Thus, another aspect of this disclosure is directed to a method of improving locomotor function after spinal cord injury in a subject in need thereof comprising the administration of AAV-rh10-NT3/chondroitinase-ABC and a pharmaceutically acceptable carrier.

Gene therapy methods are also disclosed that include the use of AAV10 to deliver neutralizing NG-2 monoclonal antibodies in combination with NT3 using AAV10-NG2Ab and AAV10-NT3 viral constructs. Thus, another aspect of this disclosure is directed to a method of improving locomotor function after spinal cord injury in a subject in need thereof comprising the administration of AAV10-NT3, AAV10-NG2Ab and a pharmaceutically acceptable carrier.

As discussed in the examples below, animals injured in a thoracic T10 contusion and lateral hemisection model received intraspinal injections of both AAV10-NG2Ab and AAV10-NT3 constructs rostral and caudal to the injury site. AAV-mediated delivery of NG2-Ab and NT3 was widespread at the injury epicenter and in distant lumbar sections of the cord. Surprisingly and unexpectedly, AAV-NG2Ab and AAV-NT3 treated animals exhibit significant improvement in locomotor function compared to control injured animals in two injury models. Thus, another aspect of the present disclosure is directed to a method of improving locomotor function after spinal cord injury in a subject in need thereof comprising the administration of AAV10-NT3 and a pharmaceutically acceptable carrier.

The animals were administered AAV10-NG2Ab and at least one of a pharmaceutically acceptable carrier, diluent and excipient during treatment. Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 mL of solution containing concentrations of from about $1 \times 10^9$ to $1 \times 10^{16}$ genomes virus vector. Another human dosage may be about $1.0 \times 10^{12}$ to about $8.0 \times 10^{12}$ genomes, or about $6.8 \times 10^{12}$ genomes. These ranges are inclusive of the endpoints and inclusive of each point within the ranges.

The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention. Further discussions can be found in U.S. Patent Publication No. 2003/0138772, which is incorporated herein by reference.

The present disclosure also relates to the use of neutralizing single chain monoclonal NG2-antibody for a period of about one day to about ten weeks, about one week to about five weeks and about two weeks to about four weeks, resulting in improved synaptic transmission after hemisection SCI. This monoclonal NG2-antibody is a mixture of two function blocking antibodies, 69 and 147 [mouse monoclonal antibodies]. Production, derivation, and specificity of two monoclonal NG2-function-neutralizing antibodies, designated as 69 and 147, and control NG2-function-non-neutralizing antibody 132 can be found in Tan A M, Colletti M, Rorai A T, Skene J H, Levine J M (2006) "Antibodies against the NG2 proteoglycan promote the regeneration of sensory axons within the dorsal columns of the spinal cord." *J. Neurosci* 26:4729-4739, which is incorporated by reference.

AAV-rh10 induced robust transduction of not only neurons, but macrophages/microglia and oligodendrocytes as well. Compared to AAV-rh10 all other vectors tested exhibited limited transduction of glial cells in damaged spinal cord (FIGS. 4A-4E, FIGS. 5A-5C; Table 1). This ability of AAV-rh10 to transduce diverse cell population in damaged spinal cord is desirable for SCI pathogenesis, which is associated with the altered function of neurons, glial cells and macrophages/microglia.

Consistent with this view, AAV-rh10 mediated delivery of NT3 combined with chondroitinase-ABC (ChABC) following T10 contusion SCI in adult rats strengthened formed connections in contused spinal cord and induced the appearance of additional detour synaptic pathways innervating dorsomedial interneurons. These improvements of transmission in animals that received AAV-rh10-NT3/ChABC treatment following contusion SCI associated with improved locomotor function. This treatment was introduced via intraspinal injections immediately after contusion SCI, but in other treatment regimens, the AAV-rh10-NT3/ChABC treatment could be delivered in any other suitable way, such as intrathecally or intramuscularly.

The compositions and methods of the present disclosure will be better understood by reference to the following Examples, which are provided as exemplary of the disclosure and not by way of limitation.

EXAMPLES

Example 1

Previous experiments have indicated that intrathecal infusion of NG2-Ab for 2 weeks, via osmotic minipump, partially improved the following deficits induced by chronic mid-thoracic lateral hemisection (HX) injury: (i) synaptic transmission to lumbar motoneurons; (ii) retrograde transport of Fluororuby (FR) anatomical tracer from L5 to L1, (iii) density of 5-HT-positive fibers and (iv) recovery of motor function after lateral hemisection SCI. A downside of administration of NG2-antibody vial mini-pump in clinics is that it requires intrathecal implantation of the catheter, which can be potentially clogged and thus limit prolonged administration of NG2-Ab. Thus the goal was to developed for clinically-relevant prolonged delivery of NG2-Ab, i.e. gene transfer of anti-NG2 monoclonal antibody.

Five adeno-associated viral vectors (AAV) (AAV-1, AAV-5, AAV-9, AAV-rh10 and AAV-hu11) serotypes encoding enhanced green fluorescent protein (GFP) transgene under control of the cyto-megalovirus (CMV) promoter, were injected intraspinally immediately after contusion spinal cord injury (150 kdyn force of IH Impactor) at T10 spinal level. Each vector was injected bilaterally, 1.2 mm rostral and 1.2 mm caudal, 1 mm lateral to midline at 1.5 mm depth, i.e. 4 intraspinal injections, 0.5 µl each (n=3-5 rats per serotype). Control group received same SCI and no injections. Animals were kept for 10 weeks; body weight and open field performance using BBB scores were evaluated weekly. At 10 weeks post-injury and AAV vectors administration, spinal cord tissue was collected and GFP signal was used to determine transduction efficacy throughout the spinal cord. Cell specific markers were used to analyze the transduction efficacy for different cell types.

Transduction of Spinal Cord at the Site of Injury/Vectors Administration

GFP signal was initially evaluated using horizontal sections of T9-T11 spinal segments, i.e. close to contusion epicenter (injury at T10). All vectors examined were effective in transduction of spinal cord tissue at the vicinity of SCI (FIG. 1). Transduction efficiency in neurons, processes and glial cells varied depending on serotype used. GFP signal and cell morphology/location were used for qualitative analyses of transduction efficiency in the vicinity of injury/vectors injections based on the modified scoring system of Cearley et al., "Expanded repertoire of AAV vector serotypes mediate unique patterns of transduction in mouse brain". *Mol Ther* 2008; 16: pages 1710-1718. This is shown in Table 1 below:

Transduction characteristics of AAV serotypes at T9-T11 segments following contusion SCI at T10 level and intraspinal injections of vectors close to injury epicenter
Scores for AAV-mediated transduction of neurons, processes and glial cells (modified from Cearley et al.)

| Serotypes | Neurons | Processes | Glial cells |
|---|---|---|---|
| AAV-1 | ++ n = 3 | ++ n = 2 | ++ n = 2 |
|  | + n = 1 | + n = 2 | + n = 2 |
| AAV-5 | +++ n = 3 | +++ n = 3 | ++ n = 3 |
|  | ++ n = 2 | ++ n = 2 | + n = 2 |
| AAV-9 | +++ n = 4 | +++ n = 4 | ++ n = 2 |
|  | ++ n = 1 | ++ n = 1 | + n = 3 |
| AAV-rh10 | +++ n = 3 | +++ n = 4 | +++ n = 4 |
|  | ++ n = 2 | ++ n = 1 | ++ n = 1 |
| AAV-hu11 | ++ n = 1 | ++ n = 1 | ++ n = 2 |
|  | + n = 2 | + n = 2 | + n = 1 |

Abbreviations:
AAV, adeno-associated virus.
Scoring:
(+) very few positive cells or processes;
(++) many positive cells or processes;
(+++) robust transduction region completely saturated with positive cells or processes.
n indicates number of animals with particular score.

As shown above, AAV serotypes 5, 9 and rh10 caused high GFP expression in cells and processes. Also as shown in Table 1, serotypes 9 and rh10 caused a high degree of transduced neurons. AAV-1, -5, -9 and -rh10 serotypes showed robust transduction of processes and AAV-rh10 showed a high number of GFP positive glial cells in white and gray matter as well as at the injury epicenter.

Qualitative Analyses of GFP Expression Throughout the Spinal Cord

Neurons.

The majority of transduced cells with neuronal morphology in the grey matter were located at the intermediate levels and in the ventral horn (FIGS. 3A-3D). Few GFP-positive cells were observed in dorsal horn of grey matter. In general, gene expression was localized mostly close to injection site and declined in distant parts of the cord. AAV-9 and AAV-rh10, however, exhibited better expression in distant lumbar and cervical spinal levels (FIG. 1). Lumbar and thoracic spinal levels possessed higher number of transduced neurons compared to cervical levels, likely due to their proximity to injection site.

Processes.

In thoracic and lumbar spinal levels many GFP positive processes were observed in lateral and ventral funiculi of white matter, with fewer GFP fibers at the dorsal funiculus (FIGS. 1 and 3A-3D). In the cervical spinal cord, GFP-positive processes were located mostly along the perimeter of white matter (FIG. 1, at arrows).

Glial Cells.

Most transduced glial cells (determined by location, size and morphology) were observed close to injury epicenter, in segments T9-T11, in both white matter and gray matter, as well as at the injury penumbra (Table 1).

Quantification of Number of Transduced Neurons

Figures 2A, 2B:
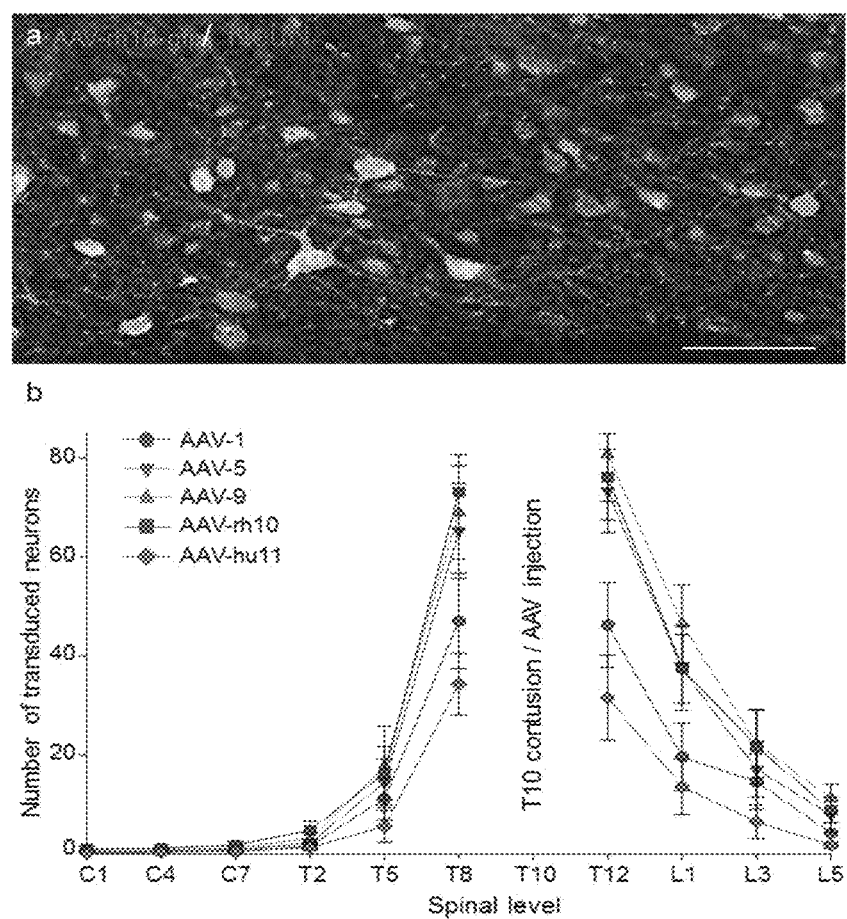
FIGS. 2A and 2B include an image and a graphical representation of the quantification of spinal cord neurons transduced by AAV-1, 5, 9, rh10, hu11 serotypes following intraspinal injections of these vectors after contusion injury at T10 spinal level.

To determine the number of transduced neurons, spinal cord sections (40 μm thick) were immunostained with neuronal marker NeuN (example of horizontal section in FIG. 2A). The number of NeuN positive cells that also showed GFP positive signal was calculated from 5 cross-sections (80 μm apart) for each spinal level from each rat (one set of Cresyl Violet stained sections was used to determine the spinal segment level; the number of NeuN labeled cells in the sections from the given segments was consistent and not significantly different (P>0.05) among all animals studied). For example, the number of NeuN-labeled cells per section was ~680-730 cells in cervical C4, ~450-490 cells at thoracic T8, ~510-560 cells at thoracic T12 and ~920-990 cells in lumbar L3 levels. Results are presented in a graph form in FIG. 2B and represent mean average number of transduced neurons per section for each serotype at different spinal levels.

The majority of transduced neurons were located approximately within 5 segments rostral and caudal to injection sites. AAV-rh10, AAV-9 and AAV-5 demonstrated high overall number of transduced neurons throughout the spinal cord.

In thoracic levels, the number of transduced neurons at T8 and T12 levels for AAV-5 (T8: 65.2±9.6; T12: 73.3±8.4; n=5 rats), AAV-9 (T8: 69.0±9.4; T12: 80.7±9.5; n=5 rats), and AAV-rh10 (T8: 73.1±7.5; T12: 76.1±8.7; n=5 rats) was significantly higher compared to AAV-1 (T8: 47.0±9.6; T12: 46.2±8.6; n=4 rats) and AAV-hu11(T8: 34.3±6.2; T12: 31.5±8.6; n=3 rats) (one way ANOVA, p<0.05). No significant difference was found between AAV-5, -9 and -rh10 at these levels. Despite some variation in the number of transduced cells, no significant difference was found in other thoracic levels between the serotypes, as graphically shown in FIG. 2B.

In lumbar levels, AAV-9 and AAV-rh10 demonstrated the highest number of transduced neurons vs. AAV-1, -5 and -hu11. No significant difference in number of transduced neurons was found between AAV-9 and AAV-rh10, as graphically shown in FIG. 2B.

In cervical levels all serotypes showed significantly lower numbers of transduced neurons compared to thoracic and lumbar segments (FIG. 2B). Overall, the highest number of transduced cells in cervical levels was observed in AAV-rh10 and AAV-9 injected animals, however no significant difference was observed between serotypes, as graphically shown in FIG. 2B.

GFP Intensity of Transduced Neurons

In order to determine the efficiency of AAV-mediated transduction of neurons, mean GFP intensity per transduced neuron were examined for each viral vector at different spinal levels. Somas of transduced cells with neuronal morphology were manually outlined and GFP intensity was measured and compared between viral vectors as described in Hutson et al., "Corticospinal tract transduction: a comparison of seven adeno-associated viral vector serotypes and a non-integrating lentiviral vector." *Gene Ther* 2011; 19: pages 49-60. Note that GFP signal was native and not amplified by immunostaining.

Figures 3A, 3B, 3C, 3D:
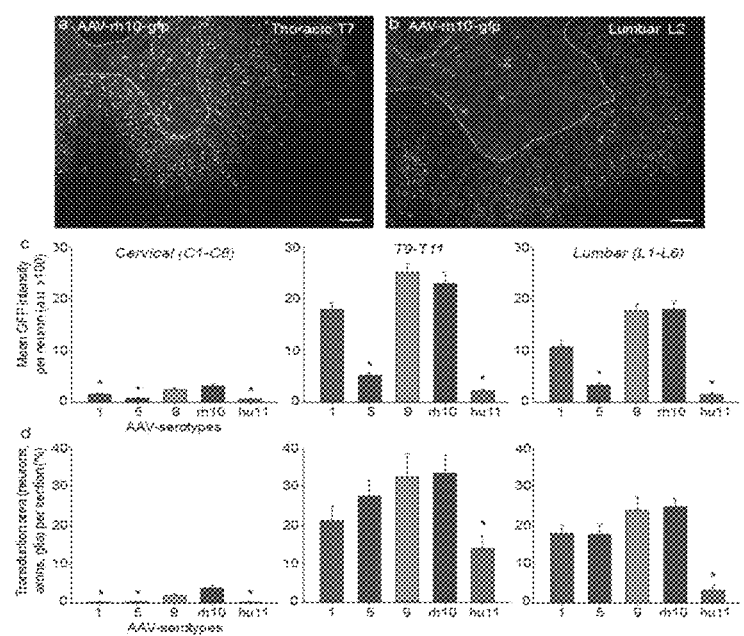
FIGS. 3A-3D include transduction characteristics (mean GFP intensity and transduction area) of AAV-1, 5, 9, rh10, hu11 serotypes following intraspinal injections after T10 contusion.

In T9-T11 levels, AAV-1, AAV-9 and AAV-rh10 showed comparable transduction characteristics, but AV-5 and AAV-hu11 serotypes demonstrated lower intensity of GFP signal per neuron compare to other serotypes (FIG. 3C). Quantification revealed a statistically significant difference in the GFP intensity per neuron between AAV-5 and -hu11 serotypes compared to other serotypes (one-way ANOVA, $P<0.05$) (FIG. 3C).

In lumbar segments quantification of GFP intensity showed a pattern similar to thoracic T9-T11 for all serotypes, with AAV-5 and AAV-hu11 demonstrating significantly lower GFP intensity per transduced neuron (FIG. 3C, one-way ANOVA, $P<0.05$).

In the cervical cord, all serotypes exhibited markedly lower intensity per transduced neuron compared to thoracic and lumbar cords. Compared to other serotypes, AAV-rh10 and AAV-9 showed significantly higher intensity per neuron (FIG. 3C).

Transduction Area

We also measured the transduction area per section at different spinal levels for each viral vector. Percentage of GFP positive area vs. total area per section was calculated and compared between viral vectors (see Methods, discussed below). Transduction area represents total transduction efficacy and therefore includes transduction of not only neurons, but processes and glial cells as well. Mean transduction area per section varied depending on viral vectors and spinal levels examined. In thoracic and lumbar segments, AAV-rh10 and AAV-9 transduced the largest areas, although with no significant difference compared to AAV-1 and AAV-5. AAV-hu11 showed significantly smaller transduced area compared to other vectors (one-way ANOVA, $p<0.05$) (FIG. 3D). In cervical spinal cord all vectors transduced markedly smaller areas compared to thoracic and lumbar levels. AAV-rh10 and AAV-9 still transduced significantly larger areas compared to all other serotypes in cervical levels (one-way ANOVA, $p<0.05$) (FIG. 3D).

Cell Type Specificity in Damaged Spinal Cord

Figures 4A, 4B, 4C, 4D, 4E:
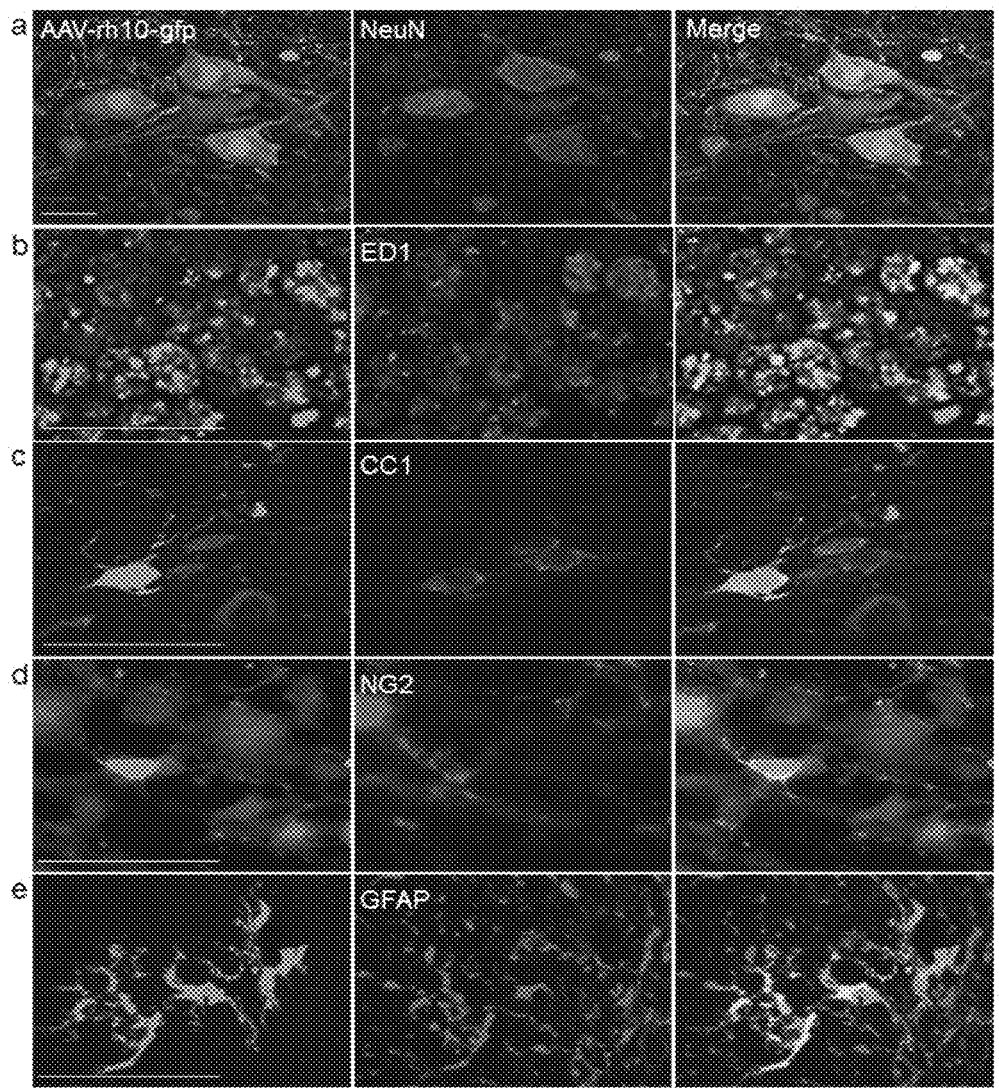
FIGS. 4A-4E include transduction of different cell types followed by intraspinal injections of AAV-rh10 after T10 contusion. Fluorescent images of T9-T11 horizontal sections were prepared 10 weeks after T10 contusion and vector administration; alternating sections were immunostained with following antibodies.

Qualitative analysis suggests that the examined vectors may transduce not only neurons but glial cells as well, with AAV-rh10 showing good results for glial cell transduction (Table 1, above). To determine which cell types could be transduced by AAV vectors, immunostaining was performed with different cell specific antibodies. Transduction of different types of cells was detected, including neurons in grey matter caudal/rostral to contusion (FIG. 4A), macrophages/microglia at the injury epicenter (FIG. 4B), oligodendrocytes in lateral and ventrolateral white matter caudal/rostral to injury (FIG. 4C), NG2-positive cells in lateral white matter caudal/rostral to injury (FIG. 4D) and astrocytes in dorsal funiculus caudal/rostral to injury (FIG. 4E).

Figures 5A, 5B, 5C:
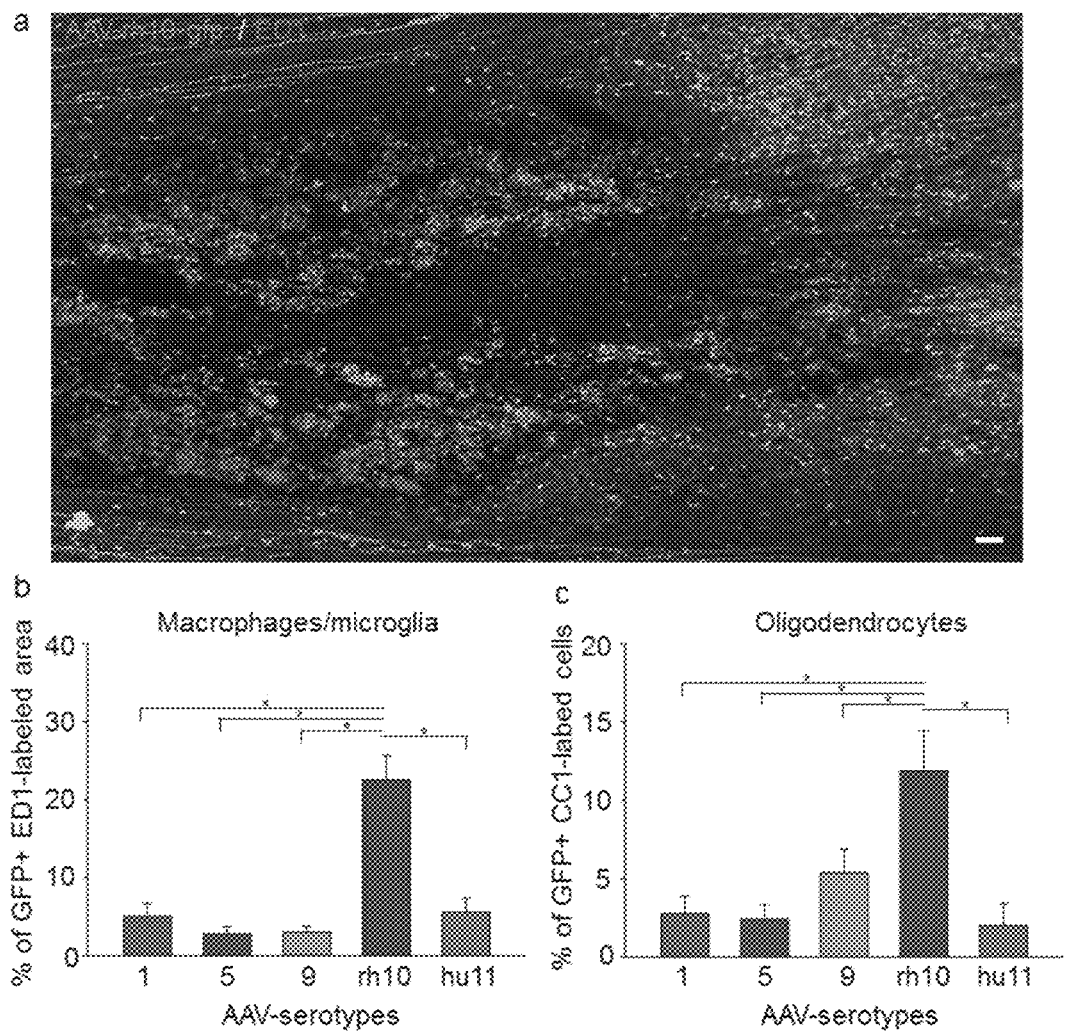
FIGS. 5A-5C include an image and data demonstrating that AAV-rh10 induced significantly better transduction of oligodendrocytes and macrophages/microglia, compared to all other serotypes, following its intraspinal administration immediately after T10 contusion.

For quantitative analyses among AAV serotypes, ED1 (to detect macrophages/microglia) and CC1 (to detect oligodendrocytes) immunostains were used. The area of ED1 positive immunoreactivity that was also positive for GFP and the percentage of GFP positive cells that were also immunolabeled with CC1 were measured (see Methods, below) and compared between all viral vectors (FIGS. 5B, 5C). AAV-rh10 had an efficient serotype, transducing ED1-positive macrophages/microglia (FIGS. 5A, 5B) and CC1-positive oligodendrocytes (FIG. 5C) compared to other serotypes.

Inflammatory Response and Behavioral Performance Following AAV Administration

The potential of the tested viral vectors to induce adverse effects upon behavioral performance and body weight, or induce additional inflammatory response following intraspinal injections of vectors after T10 contusion were examined. In order to accomplish this examination, groups of animals that received contusion SCI and intraspinal AAV injections were compared with a control group that received the same contusion injury and no injections.

Figures 6A, 6B, 6C, 6D:
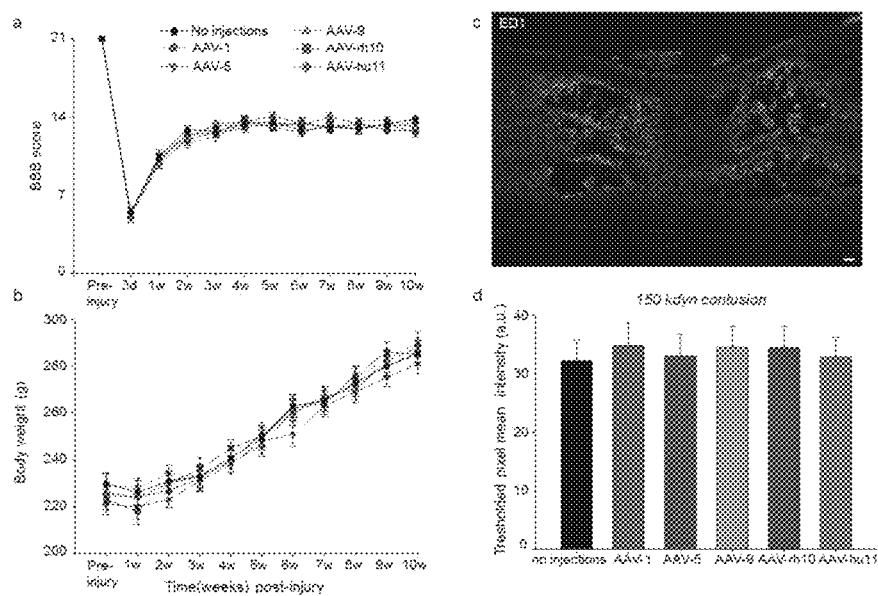
FIGS. 6A-6D are an image and data representing that injections of AAV viral vectors following contusion SCI did not induce additional changes in behavioral performance, body weight, or macrophage/microglial response.

Animals from all groups demonstrated similar trends of body weight gain and similar pattern of recovery in open field BBB test, reaching a plateau after 3 weeks post injury. No significant difference in behavioral performance or cellular inflammatory response was observed at any time point between animals that received contusion injury and intraspinal injections of either AAV-1, -5, -9, -rh10 or -hu11 viral vectors and animals with contusion spinal cord injury and no injections (FIGS. 6A, 6B).

Immunochemistry experiments using a macrophage/microglia marker ED1 revealed that none of viral vectors administered intraspinally following contusive SCI generated additional macrophage/microglia response (FIG. 6C, 6D), known as an index of cellular inflammatory response following SCI in rats.

Materials and Methods for Example 1

AAV Viral Vectors

All AAV vectors encoding enhanced green fluorescent protein (GFP) gene and expressing cyto-megalovirus (CMV) promoter (AAV.CMV.PI.EGFP.WPRE.bGH) have been provided by Penn Vector Core at the University of Pennsylvania. AAV 1, 5, 9, rh10 and hu11 serotypes used in this study have been constructed by incorporating different viral capsid proteins into the AAV2 recombinant genome. All AAV vectors tested in this study have been adjusted to have equivalent dosages of genome copies ($6.8 \times 10^{12}$ GC/mL).

Spinal Cord Injury and Vector Delivery

All procedures were approved by the Institutional Animal Care and Use Committee at SUNY-Stony Brook and Northport VAMC. Adult, female Sprague Dawley rats (~220 g; Taconic Farms, Germantown, N.Y.) were deeply anesthetized with 3% isoflurane in 100% $O_2$ followed by 1.5% isoflurane in 100% $O_2$ to maintain an anesthetic state during surgery. Rats were given an injection of Buprenorphine (0.01 mg/kg) prior to surgery to reduce post-operative pain and placed on a water circulating heat pad. Body temperature was monitored by a rectal thermometer and maintained at 36-37° C. Dorsal laminectomy was performed to expose the dorsal surface of T10 spinal cord. Contusion injuries (150 kDyn force) were performed using an IH-0400 Impactor device (Precision System and Instrumentation, Lexington, Ky.). Following the injury, animals received one of five AAV serotypes (AAV-1, 5, 9, rh10, or hu11) as intraspinal injections. Specifically, 4 intraspinal injections of 0.5 μL each were made into the left and right spinal cord, 1 mm lateral of midline at 1.5 mm depth, 1.2 mm rostral and 1.2 mm caudal to injury epicenter. Following the injury and vector injections, muscles and skin were closed and subcutaneous injections of antibiotic (Baytril 5 mg/kg) and 5 mL of sterile lactated Ringer's solution were administered. The rats were housed individually and received injections of Baytril, Buprenorphine and lactated Ringer's for 3 days following surgery.

Tissue Processing and Immunohistochemistry

Ten weeks post injury and AAV administration, rats received an overdose bolus of urethane and were transcardially perfused with 400 mL of 4% paraformaldehyde in 0.1 M PBS. Spinal cords were removed and post-fixed 1-2 hours in 4% paraformaldehyde followed by cryoprotection for a minimum of 48 hours in a 30% sucrose solution. Following cryoprotection, spinal cord segments were cut rostro-caudally on a cryostat at a thickness of 40 µm, and sections were collected serially onto Colorfrost Plus slides (ThermoFisher Scientific) in seven sets. Segments T9-T11, containing the injury site, were sectioned horizontally. The remainder of cervical, thoracic, and lumber segments (C1-T8 and T12-L6) was sectioned in the transverse plane.

One complete set was stained with Cresyl Violet and used to confirm the spinal cord segment level as well as for injury reconstruction. The remaining sets were used for quantitative analysis and immunofluorescence staining to identify transduced cell types. Various cell specific antibodies were used for immunofluorescence studies: mouse anti-CD68 (ED1) (1:200; Abcam, Cambridge, Mass.) to detect macrophages/microglia, mouse anti-APC (CC1) (1:100; Abcam, Cambridge, Mass.) to detect oligodendrocytes, mouse anti-NeuN (1:600; Millipore, Billerica, Mass.) to detect neurons, rabbit anti-GFAP (1:500; Dako, Carpinteria, Calif.) to detect astrocytes and rabbit anti-NG2 (1:500; antibody generously supplied by Dr. Joel Levine) to detect NG2. Briefly, sections were blocked in 0.1 m PBS containing 6% normal goat serum and 0.3% Triton X-100 and then incubated overnight at 4° C. in one of the above antibodies. After rinsing several times with 0.1 m PBS, sections were incubated at room temperature in either goat-anti-mouse or goat-anti-rabbit secondary antibody (Alexa Fluor 594, Invitrogen; 1:800 dilution) for 1 hour. Sections were then rinsed in PBS, dipped briefly in $dH_2O$, and cover slipped with (Fluoromount-G; Southern Biotech, Birmingham Ala.). A Zeiss Axioskop2 microscope and an Olympus Fluoview FV1000 confocal microscope were used to analyze and collect images.

Quantitative Analysis

Total Number of Transduced Neurons.

Quantitative analysis was performed by researchers who were blinded to the AAV serotypes of the cases under review. The total number of transduced neurons at different spinal levels was obtained by manually counting all cells exhibiting co-localization of GFP and NeuN signal in 5 cross-sections separated by 80 µm at each spinal level (C1-T8 and T12-L6).

GFP Intensity.

All images that were used to measure GFP intensity were captured with a Zeiss AxioCam MRm camera using identical settings. A maximum of 10 randomly selected transduced cells with neuronal morphology in grey matter in all sections of one complete series were manually outlined and the mean GFP intensity was measured using Zeiss Axiovision v4.8 software.

Transduction Area.

Transduced area per section for one complete set was measured using ImageJ software (National Institute of Health). Thresholded pixel area was calculated by eliminating background and quantifying only GFP positive signal area. The resulting value was divided by the total area of the section to give the percentage of GFP positive area per section.

ED1 Immunoreactivity.

To quantify ED1 immunoreactivity, one complete set of horizontal sections from the T9-T11 segment, containing the injury epicenter, for each rat was immunostained with ED1. Images were captured using identical settings and ED1 positive signal was calculated after thresholding and eliminating background intensity using ImageJ software. To compare the number of transduced macrophages/microglia between serotypes, the area of GFP positive cells that were also immunolabeled with ED1 was measured and percent out of total area of ED1 positive immunoreactive cells was calculated at the injury epicenter within a fixed ($1 \times 0.7$ mm$^2$) area for each section.

CC1 Immunoreactivity.

To compare the number of transduced oligodendrocytes, one complete set from the T9-T11 segment was immunostained with anti-APC (CC1) antibody and the percent of cells that were positive for both GFP and CC1 signal out of the total number of cells immunostained with CC1 was calculated within four fixed ($0.5 \times 0.3$ mm$^2$ each) areas bilaterally within intact white matter just rostral and caudal to injury, for each section.

Behavioral Performance and Body Weight

In order to examine the effects of intraspinal injections of AAV vectors on behavioral performance and body weight, animals from AAV serotype groups were compared with a group of animals that received the contusion spinal cord injury but no AAV injections. Open field Basso-Beattie-Breshnahan (BBB) score was used to assess behavioral performance. Body weights of all rats were monitored and compared between groups. Baselines for BBB and body weigh were determined prior to injury, then recorded 3 day post-injury and weekly.

Statistical Analysis

Data were analyzed using SigmaPlot 11.0 software (Systat Software Inc., San Jose Calif.). A one-way ANOVA or one-way ANOVA on ranks followed by Tukey's or Dunn's multiple comparisons post-hoc tests were used to compare the data. Results were considered statistically significant for $P<0.05$. Data are means±SE.

Example 2

Expression pattern of six AAV serotypes were compared—the results indicated that AAV-10 serotype induced the best transduction of spinal cord tissue following contusion SCI. Abovementioned experiments have demonstrated that AAV-rh10 induces robust transduction of both neuronal and glial cells in chronically contused rats. Even though efficacy to transduce neurons was comparable to established AAV-1, -5 and -9 serotypes, AAV-10 transduced significantly higher numbers of macrophages/microglia and oligodendrocytes. These results indicated that adeno-associated vector (serotype 10; AAV10) may be an appropriate tool for prolonged administration of NG2 antibody to damaged spinal cord and are discussed below in reference to Examples 2 and 3.

Figures 7A, 7B, 7C, 7D, 7E:
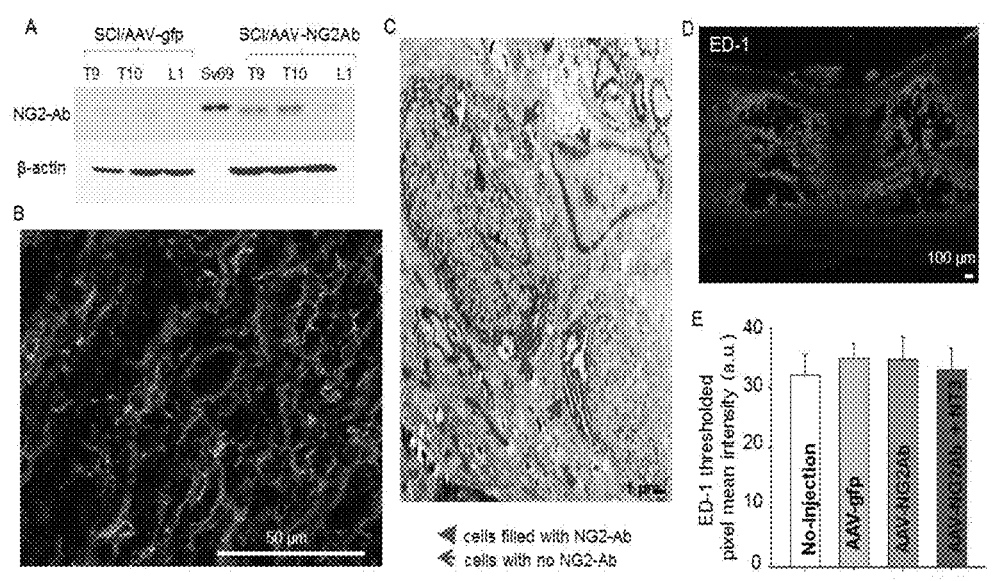
FIGS. 7A-7E are images and data of AAV10-NG2Ab in contused spinal cords.

FIGS. 7A-7E illustrate AAV10-NG2Ab in contused spinal cords. Results suggest the expression of NG2-Ab in the vicinity of contusion injury, as shown in FIGS. 7A-7E. FIG. 7A is an image of western blots of purified NG2-Ab (Sv69) and AAV-mediated expression of NG2-Ab in contused cords injected with AAV-gfp and AAV-NG2Ab. The NG2-Ab amino acid sequence is shown as SEQ ID NO. 1. As can be seen from SEQ ID NO. 1, the sequence includes a signal sequence at the N-terminal, a linker GGGGSGGGGSGGGGS and a C-terminal his tag. The nucleotide sequence encoded by SEQ ID NO. 1 is included below as SEQ ID NO. 2.

FIG. 7B is an image of AAV10-mediated expression of NG2-Ab in close proximity to NG2-positive (lighter portion) cells and processes Immunochemistry experiments revealed presence of the expressed NG2-Ab in close proximity to NG2 in cells and processes in the vicinity of contusion injury, i.e. in the areas where the level of NG2 is upregulated in FIG. 7B. FIG. 7C is an electron-microscope image to confirm expression of NG2-Ab in cells. FIGS. 7D and 7E are an image and summarized data of intraspinal injections of AAV-NG2Ab alone, or with AAV-NT3. These images demonstrate that AAV-NG2Ab alone, or with AAV-NT3 did not generate additional macrophage/microglia response.

Figures 8A, 8B, 8C, 8D, 8E:
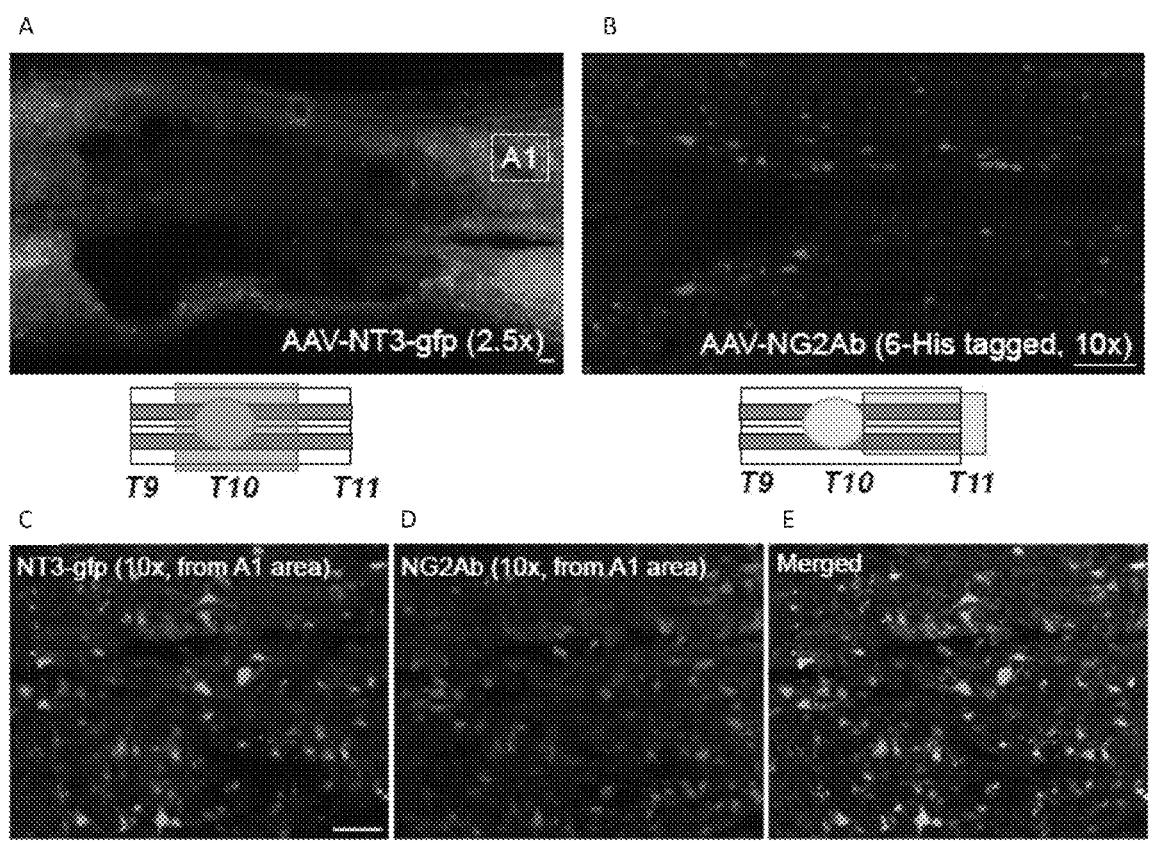
FIGS. 8A-8E are images demonstrating transduction of spinal cord tissue following intraspinal injections of AAV10-NT3-gfp and AAV10-NG2Ab.

FIGS. 8A-8E demonstrate robust transduction of spinal cord tissue following intraspinal injections of AAV10-NT3-gfp and AAV10-NG2Ab. FIGS. 8A and 8B are images of horizontal sections of T9-T11segments; gfp signal was used to visualize AAV mediated delivery of NT3 co-expressing gfp and immunostaining with anti-6-His to detect 6-His tagged NG2-Ab. FIGS. 8C and 8D are images of many cells in grey matter close to SCI transduced with NT3-gfp and NG2-Ab. FIG. 8E is a merged image showing colocalization of NT3 and NG2-Ab in many cells. Scale bars are 100 μm.

Experiments were conducted using intraspinal injections of AAV10-NG2Ab and AAV10-NT3-gfp in adult rat spinal cord following contusion SCI to review whether expressing NG2-Ab specifically bind to NG2-positive and other cells in spinal cord tissue.

Results suggest the expression of NG2-Ab in the vicinity of contusion injury, as shown in FIG. 7A-7E. Immunochemistry experiments revealed presence of the expressed NG2-Ab in close proximity to NG2 in cells and processes in the vicinity of contusion injury, i.e. in the areas where the level of NG2 is upregulated (FIG. 7B). Electron-microscopy images additionally confirm expression of NG2-Ab in cells (FIG. 7C). Experiments, using a macrophage/microglia marker ED-1, revealed that administration of AAV10-NG2Ab alone or together with AAV10-NT3 following contusive SCI did not generate additional macrophage/microglia response (FIGS. 7D, 7E), known as an index of cellular inflammatory response following SCI in rats. AAV10-NT3-gfp and AAV10-NG2Ab were observed to mediate robust transduction of spinal cord tissue (FIG. 8A-8E). AAV10-NG2Ab mediated delivery of NG2-Ab to many types of cells was shown to induce neurons in grey matter caudal/rostral to contusion (FIG. 9A), oligodendrocytes, including lateral and ventrolateral white matter close to injury (FIG. 9B) and microglia/macrophages at the injury epicenter (FIG. 9c).

Figures 9A, 9B, 9C:
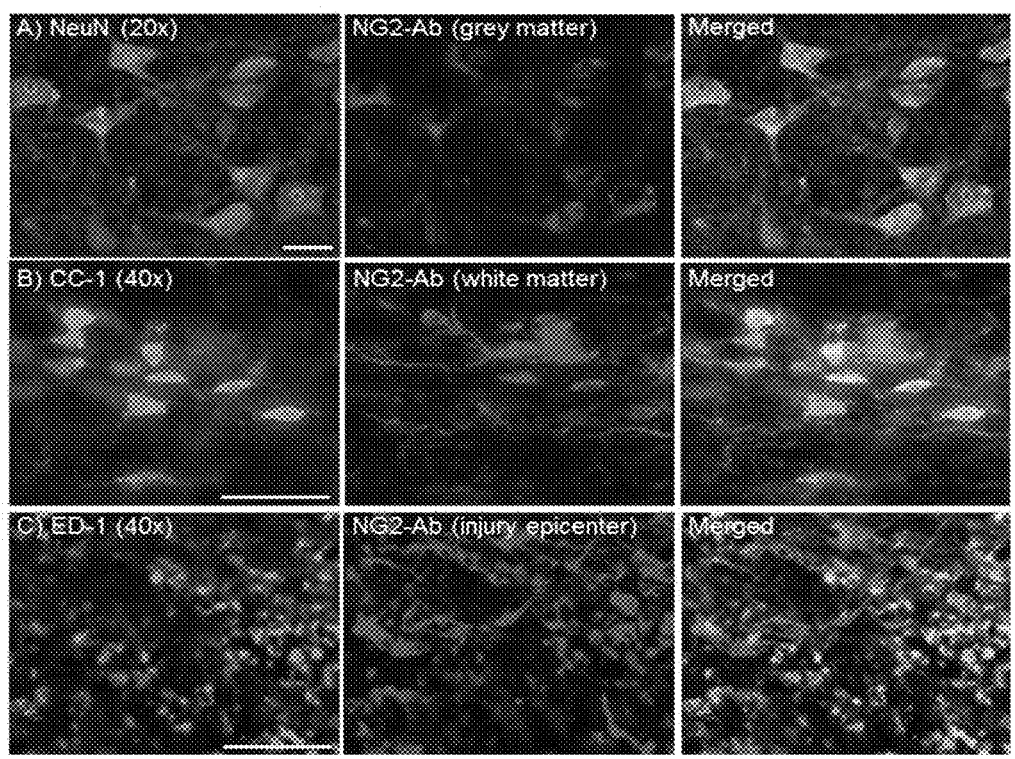
FIGS. 9A-9C are images demonstrating the transduction of axons and different types of cells following intraspinal injections of AAV-NG2Ab.

FIGS. 9A-9C illustrate transduction of axons and different types of cells following intraspinal injections of AAV-NG2Ab in injured spinal cord.

FIGS. 9A-9C are images of T9-T11 horizontal sections of T10 contused spinal cord immunostained with neuronal marker NeuN, olygodendrocyte marker CC-1, macrophage/microglia marker ED-1 and anti-6-His (to detect NG2-Ab) demonstrating transduced neurons in the grey matter, oligodendrocytes in white matter and macrophages/microglia in the injury epicenter. Scale bars are 50 μm.

Figure 10:
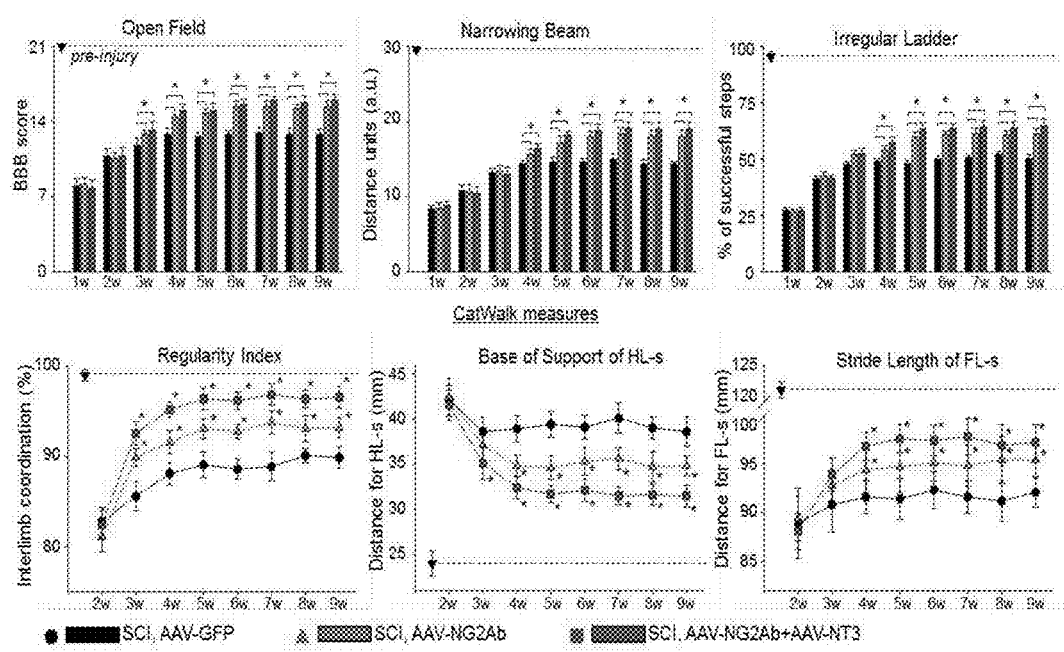
FIG. 10 is data representing locomotor function after contusion and treatment with AAV-NG2Ab and AAV-NG2Ab plus AAV-NT3.
Figures 11A, 11B, 11C:
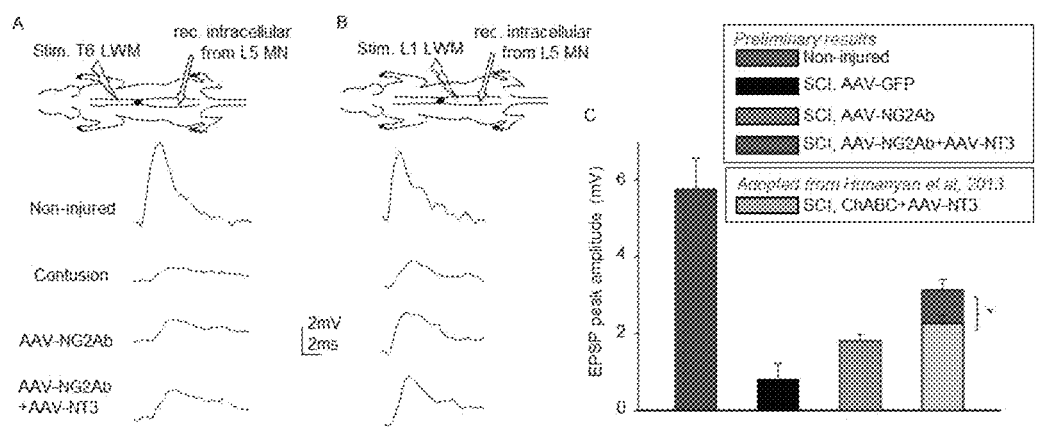
FIGS. 11A-11C are data representing the electrophysiological evaluation of transmission.

These experiments indicate that intraspinal injections of AAV10-NG2Ab immediately following moderate (150 kdyn) mid-thoracic contusion SCI improved recovery of locomotor function, as shown in FIG. 10. These improvements of function associated with strengthened transmission in spinal circuitry in AAV10-NG2Ab injected rats (FIG. 11A-11C). The greatest improvements of both transmission and motor function were seen in animals that received treatment with AAV10-NG2 combined with AAV10-NT3 (FIGS. 10, 11A-11C).

Results of electrophysiological and behavioral experiments reported recently were compared with corresponding results from the present experiment. Comparisons revealed that intraspinal injections of AAV10-NG2Ab/AAV10-NT3 after contusion SCI induced significantly better improvement of synaptic transmission (FIG. 11C) and locomotor function (FIGS. 12A and 12B) than intraspinal injections of ChABC/AAV10-NT3 in the identical SCI model. Morover, AAV-NG2Ab mediated delivery of NG2-Ab after contusion SCI induced prolonged improvements of ground locomotion (BBB scoring, FIG. 10), vs recently reported results transient improvement of BBB scores by NG2-Ab administered via osmotic minipump after lateral hemisection (HX).

FIGS. 10, 11A-11C and FIGS. 12A and 12B are further discussed below.

FIG. 10 illustrates treatment with AAV-NG2Ab and AAV-NG2Ab plus AAV-NT3 improved locomotor function after contusion (150 kdyn) SCI. Recovery in BBB, two challenging tests (Narrowing beam, Irregular ladder) and CatWalk gait. Data presented as mean±SE. *P<0.05. n=6/group.

FIGS. 11A-11C illustrate electrophysiological evaluation of transmission through injury epicenter (FIG. 11A) and in segments caudal to the injury (FIG. 11B). Intracellular recording from L5 motoneurons in animals after completion of behavioral testing described in FIG. 10. AAV-NG2Ab strengthened transmission in contusive spinal cord. AAV-NG2Ab combined with AAV-NT3 induced further improvements of transmission through axons spanning injury epicenter and within segments caudal to injury. FIG. 11C is a summary of results and comparison of EPSP responses evoked from T6 and measured in AAV-NG2Ab plus AAV-NT3 contusive group with previously reported results in rats that received identical T10 contusion and treatment with ChABC plus AAV-NT3. Data presented as mean±SE. *P<0.05. n=6/group.

Figures 12A, 12B:
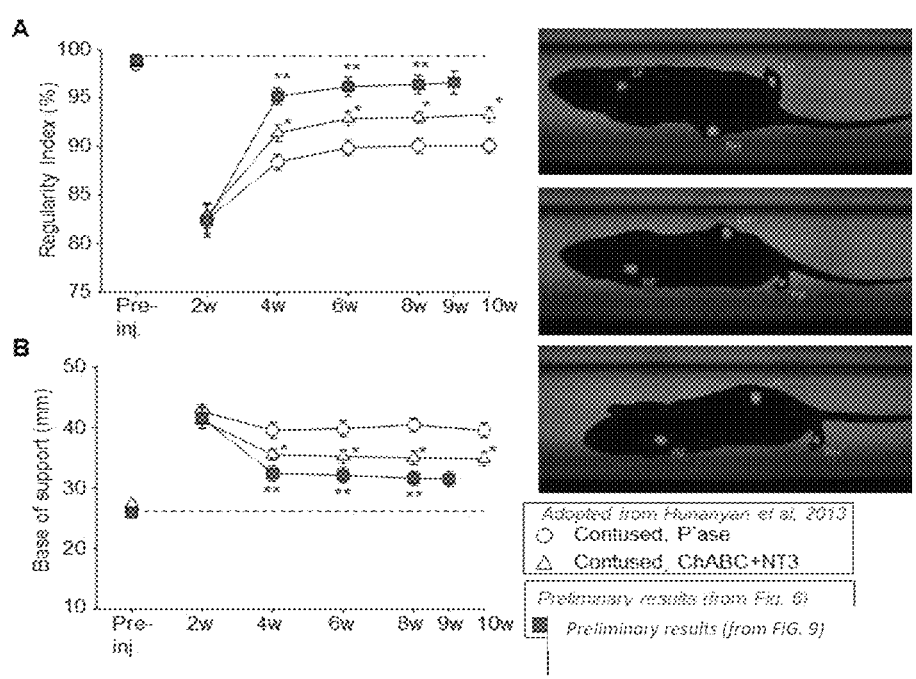
FIGS. 12A and 12B are data and images comparing catwalk gait parameters measured in a AAV-NG2Ab plus AAV-NT3 contusive group.

FIGS. 12A and 12B are comparisons of Catwalk gait parameters (Regulatory Index and Base of Support) measured in AAV-NG2Ab plus AAV-NT3 contusive group (FIG. 10) with these parameters previously reported for rats that received identical T10 contusion and treatment with ChABC plus AAV-NT3. *P<0.05: penicillinase vs. ChABC+AAV-NT3**P<0.05: AAV-NG2Ab+AAV-NT3 (from FIG. 10) vs. ChABC+AAV-NT3.

Example 3

Figure 13:
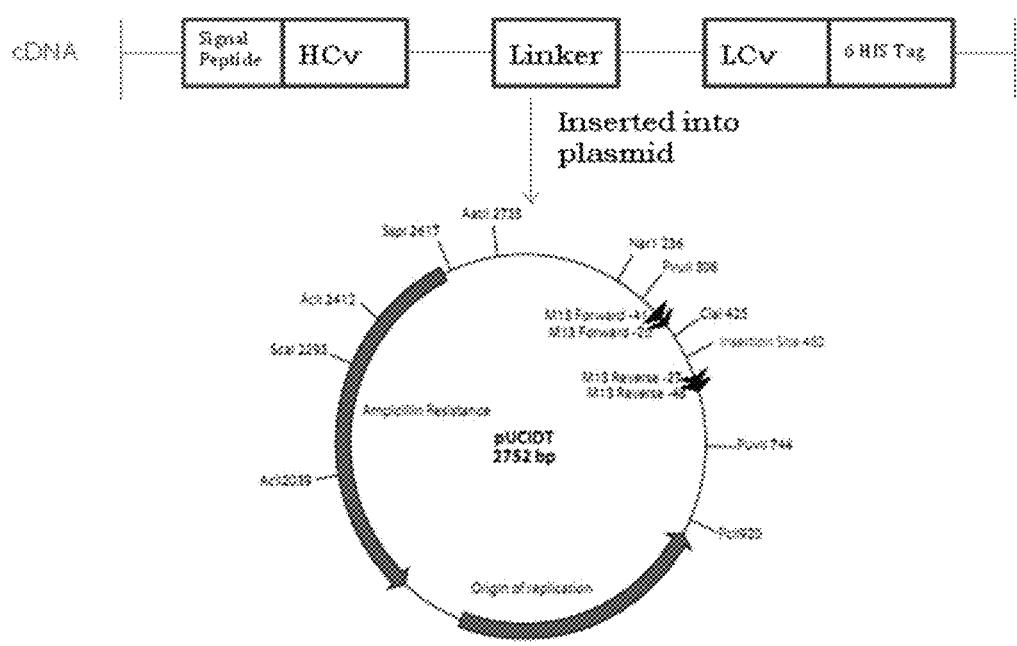
FIG. 13 is a graphical representation of how the NG2 antibody incorporating the expression signal was made.

Thus, new tools have been developed for clinically-relevant prolonged delivery of NG2-Ab, i.e. gene transfer of anti-NG2 monoclonal antibody using adeno-associated vector (serotype 10; AAV10). The cDNA construct for NG2-Ab has been created, comprising a signal peptide, heavy chain variable region, linker region consisting of serines and glycines, light chain variable region, and a 6 histidine tag, as illustrated in FIG. 13. The cDNA was then inserted into a plasmid by Integrated DNA technologies.

Figure 14:
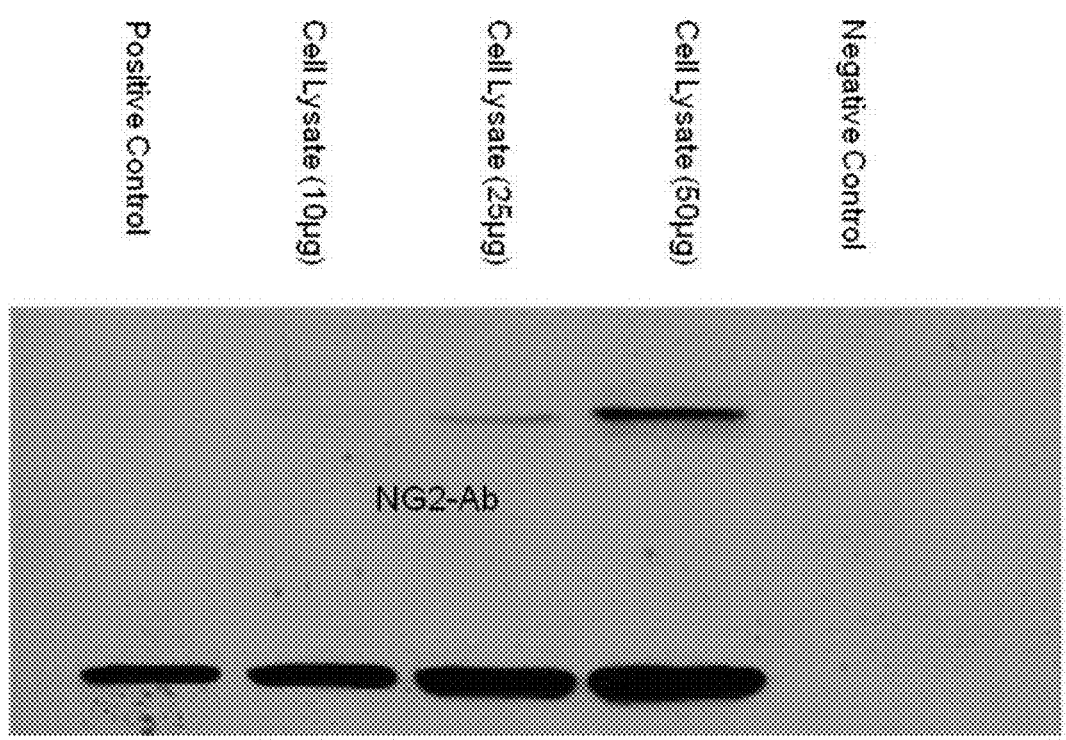
FIG. 14 is an image of a Western Blot analysis.
Figure 15:
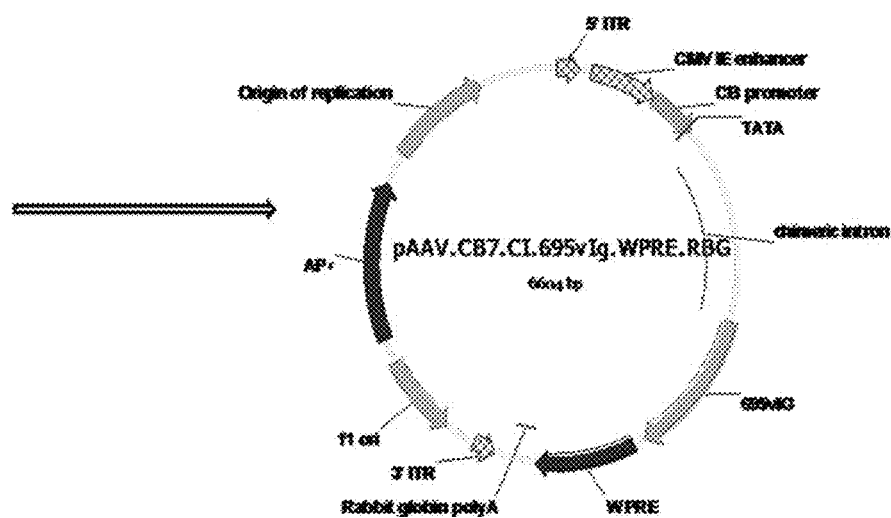
FIG. 15 is a graphical representation of the constructed AAV10-NG2Ab vector.

HEK293 cells were transfected and expression of NG2-Ab has been confirmed, as shown in FIG. 14. FIG. 14 is a Western Blot analysis of the NG2-AAV antibody expressed in HEK293T cells. HEK293T cells were transiently transfected with 69slvg DNA. Media and cell lysate were collected 48 hours after transfection for analysis. Samples were performed on a 10% SDS-Page gel. Proteins were visualized with anti HIS tag antibody, and an ECL mouse IgG, HRP-linked secondary antibody. cDNA for NG2-Ab and the plasmid, were then sent to the PENN vector core, where they were successfully inserted into AAV-10 viral vector, as illustrated in FIG. 15.

The effects of AAV10-mediated delivery of NG2-Ab in rats after HX and contusion SCI was then reviewed. Experiments using intraspinal injections of AAV10-NG2Ab combined with AAV10 vector expressing neurotrophin 3 (AAV10-NT3-gfp) were conducted in adult rat spinal cord following HX and contusion SCI. A number of behavioral tests to assess effects of treatment on locomotor function were conducted.

To evaluate effects of treatments the following tests have been carried out: Irregular Ladder, Narrowing Beam and Catwalk gait analysis. Prior to injury, animals were trained to cross the Ladder, Beam and Catwalk runways. Data regarding these results are discussed on connection with FIG. 16 and FIG. 17.

Figure 16:
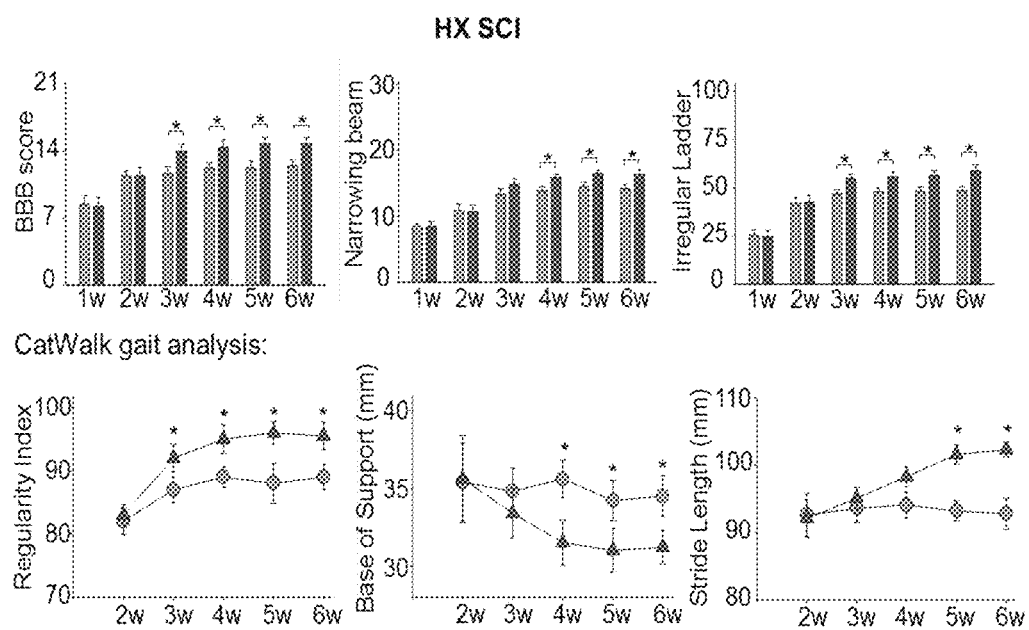
FIG. 16 illustrates that treatment with AAV-NG2Ab plus AAV-NT3 improved locomotor function after HX SCI.

FIG. 16 illustrates that treatment with AAV-NG2Ab improved locomotor function after HX SCI. Recovery in Basso, Beattie and Bresnahan (BBB) locomotor scale included three tests (Narrowing beam and Irregular ladder) and CatWalk gait. Data presented as mean±SE*P<0.05, n=6/group. The darker data bars and the dark triangle data points represent AAV-NG2Ab results, the lighter data bars and the lighter circular data points represent AAV-gfp.

Figure 17:
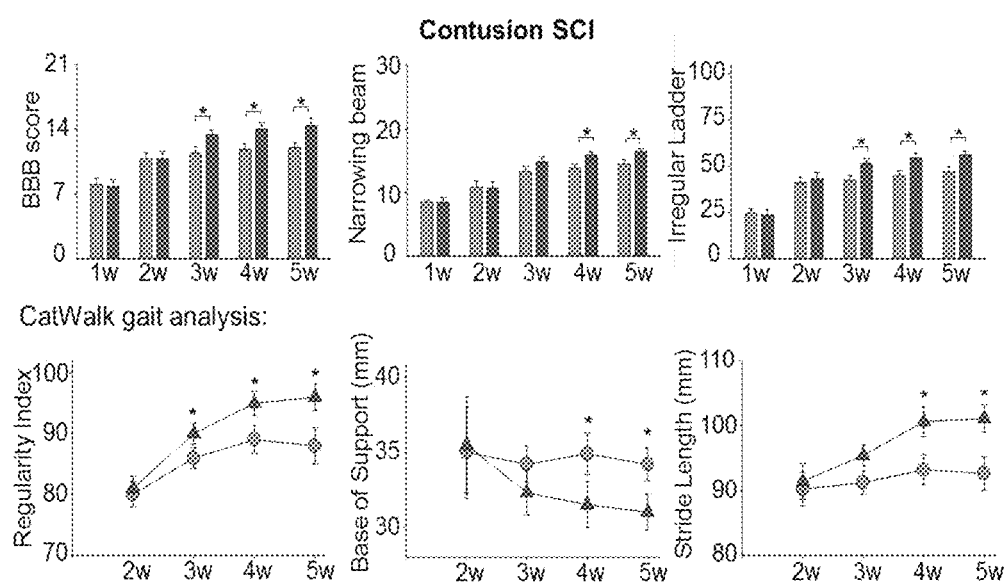
FIG. 17 illustrates that treatment with AAV-NG2Ab plus AAV-NT3 improved locomotor function after contusion SCI.

FIG. 17 illustrates that treatment with AAV-NG2Ab improved locomotor function after contusion SCI. n=6/group. The darker data bars and the dark triangle data points represent AAV-NG2Ab results, the lighter data bars and the lighter circular data points represent AAV-gfp.

The results illustrated in FIG. 16 and FIG. 17 were gathered as discussed below. Rats were observed in an open field and BBB testing was carried out by two independent observers for 4 minutes. Joint movements, weight support, paw placement and coordination were evaluated according to the 21-point BBB locomotion scale.

For the Irregular Ladder data, the animals were required to cross a 1-meter long horizontal ladder elevated 30 cm above the ground. A defined stretch of 60 cm was chosen for analysis. To prevent habituation to a fixed bar distance, the bars in this sector were placed irregularly (1-4 cm spacing). The animals crossed the Ladder Rung Walk twice in the same direction and once in the opposite direction. The number of errors (any kind of foot slip or total miss) was divided by the total number of steps in each crossing, yielding the percentage of missteps.

For the Narrowing Beam data, the ability of the rats to balance across a tapered beam 20 cm above the ground was assessed. The beam is graded into 30 stretches of the same length, but different width, starting with 5 cm and ending with 1.5 cm width and can be crossed easily by an intact animal. The maximum possible score in this test is 30. The unit at which the first slip of either hind limb was made was counted and normalized for three runs.

For the CatWalk data, locomotor function was completed using the CatWalk device (Noldus Information Technology) Animals crossed the runway where their footprints were captured by a high-speed camcorder. Data from 3 complete uninterrupted runs for each animal were collected and analyzed using CatWalk XT software. Gait parameters, such as Regularity Index and Base of Support, were collected and compared between groups. These parameters have been reported as objective measurements of locomotor performance and coordination after spinal cord injury.

The results illustrated in FIGS. 16 and 17 suggest that treatment with AAV10-NG2Ab improved locomotor function following HX (FIG. 16) and contusion (FIG. 17) SCI.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. An adeno-associated viral vector monoclonal antibody construct AAV10-NG2Ab of SEQ ID NO. 1.

2. A method of improving locomotor function after spinal cord injury in a subject in need thereof comprising the administration of AAV10-NG2Ab and a pharmaceutically acceptable carrier.

3. The method of any claim 2 wherein said administration is intraspinal.

4. The method of claim 2, wherein the AAV10-NG2Ab is administered in an amount of about $1.0 \times 10^{12}$ to about $8.0 \times 10^{12}$ GC/mL.

5. The method of claim 2, wherein the AAV10-NG2Ab is administered in an amount of about $6.8 \times 10^{12}$ GC/mL.

6. The method of claim 2, wherein the administration occurs for about one day to about ten weeks.

7. The method of claim 2, wherein the administration occurs for about one week to about five weeks.

8. The method of claim 2, wherein the administration occurs for about two weeks to about four weeks.

9. A composition, the composition comprising a therapeutically effective amount of AAV10-NG2Ab and at least one of a pharmaceutically acceptable carrier, diluent and excipient.

10. A method of improving locomotor function after spinal cord injury in a subject in need thereof comprising the administration of AAV10-NT3, AAV10-NG2Ab and a pharmaceutically acceptable carrier.

* * * * *